United States Patent [19]

Walker

[11] Patent Number: 4,751,344
[45] Date of Patent: * Jun. 14, 1988

[54] CATALYTIC SYNTHESIS OF OLEFINS FROM PARAFFINS

[75] Inventor: Howard W. Walker, Baton Rouge, La.

[73] Assignee: Ethyl Corporation, Richmond, Va.

[*] Notice: The portion of the term of this patent subsequent to Jun. 2, 2004 has been disclaimed.

[21] Appl. No.: 37,231

[22] Filed: Apr. 16, 1987

Related U.S. Application Data

[63] Continuation-in-part of Ser. No. 859,696, May 5, 1986, Pat. No. 4,670,621.

[51] Int. Cl.$^4$ .................................................. C07C 5/02
[52] U.S. Cl. ..................................... 585/656; 585/257; 585/277; 585/440; 585/616; 585/660; 585/661
[58] Field of Search ............... 585/656, 616, 660, 661, 585/257, 277, 440

[56] References Cited

U.S. PATENT DOCUMENTS

| | | | |
|---|---|---|---|
| 3,524,898 | 8/1970 | Beirne | 585/660 |
| 3,849,510 | 11/1974 | Maspero | 585/660 |
| 4,322,556 | 3/1982 | Patterson | 585/660 |
| 4,359,594 | 11/1982 | Patterson | 585/434 |
| 4,361,497 | 11/1982 | Boldt | 585/645 |
| 4,511,745 | 4/1985 | Bergman | 570/241 |
| 4,670,621 | 6/1987 | Walker | 585/656 |

OTHER PUBLICATIONS

Crabtree, Chem. Rev., 1985, vol. 85, pp. 245-269.
Felkin et al., Tetrahedron Letters, 1984, vol. 25(12), pp. 1279-1282.
Baudry et al., Tetrahedron Letters, 1984, vol. 25(12), pp. 1283-1286.
Crabtree et al., J. Am. Chem. Soc., 1979, 101:26, pp. 7738-7740.
Baudry et al., J.C.S. Chem. Comm., 1980, pp. 1243-1244.
Baudry et al., J. Chem. Soc., Chem. Commun., 1982, pp. 606-607, 1235-1236.
Baudry et al., J. Chem. Soc., Chem. Commun., 1983, pp. 788-789.
Aktogu et al., Bull. Soc. Chim. France, 1985, (3), pp. 381-385.
Crabtree et al., J.C.S. Chem. Comm., 1981, pp. 1217-1218.
Crabtree et al., J. Am. Chem. Soc., 1984, 106, pp. 2913-2917.
Burk et al., Organometallics, 1984, (3), pp. 816-817.
Burk, J. Chem. Soc., Chem. Commun., 1985, pp. 1829-1830.
Crabtree et al., J. Am. Chem. Soc., vol. 104, pp. 108-113, 6994-7001, (1982).

Primary Examiner—Asok Pal
Attorney, Agent, or Firm—John F. Sieberth

[57] ABSTRACT

Saturated hydrocarbon is transformed catalytically into olefinic hydrocarbon of corresponding skeletal configuration by reacting the saturated hydrocarbon with a suitable alkene cyclopentadienyl or alkene arene transition metal molecular complex, such as bis(ethylene)pentamethylcyclopentadienyliridium, bis(ethylene)pentamethylcyclopentadienylrhodium and bis(ethylene)-hexamethylbenzene osmium in the presence of free alkene as hydrogen acceptor. The reaction may be performed photochemically under irradiation with ultraviolet light or it may be performed thermolytically under application of heat. The catalyst may be charged to the reaction as a preformed alkene cyclopentadienyl or alkene arene transition metal molecular complex or the catalyst may be formed in situ in the reaction mixture via displacement of ligand from a suitable transition metal complex containing the displaceable ligand, such as dicarbonylpentamethylcyclopentadienyliridium or cyclooctadienepentamethylcyclopentadienyliridium.

22 Claims, No Drawings

CATALYTIC SYNTHESIS OF OLEFINS FROM PARAFFINS

This is a continuation-in-part of prior copending application Ser. No. 859,696, filed May 5, 1986, now U.S. Pat. No. 4,670,621.

In one of its forms this invention relates to activating carbon-hydrogen bonds of a saturated hydrocarbon with an alkene (e.g., ethylene) molecular complex of a transition metal in the presence of gaseous ethylene or other alkene or cycloalkene so that olefinic hydrocarbon corresponding in skeletal configuration to the saturated hydrocarbon is formed. When ethylene is employed, ethane is coproduced in the process, and thus ethylene is caused to serve as a hydrogen acceptor. This was a singularly unexpected discovery. Ethylene has been regarded heretofore as an ineffective hydrogen acceptor in attempts to dehydrogenate alkanes with transition metal complexes. See R. H. Crabtree, "The Organometallic Chemistry of Alkanes", *Chem. Rev.*, 1985, 85, 245–269, page 253. Indeed, t-butylethylene was previously considered to be one of the very few olefins that is an effective hydrogen acceptor in reactions of this type, and according to Crabtree (loc. cit.) its usefulness "was only discovered after an extensive search".

Pursuant to another embodiment of this invention, saturated hydrocarbon (i.e., paraffin or cycloparaffin or both) is transformed catalytically to olefinic hydrocarbon by transferring hydrogen from the saturated hydrocarbon to a free alkene via an alkene cyclopentadienyl transition metal molecular complex or an alkene arene transition metal molecular complex so that olefinic hydrocarbon corresponding in skeletal configuration to the saturated hydrocarbon is formed. In essence, the paraffinic or cycloparaffinic carbon-hydrogen bonds are transformed into the activated carbon-hydrogen bonds of the catalyst and thence are transferred to the free olefin serving as the hydrogen acceptor. Because of the catalyst employed, it is now deemed possible to use alkenes in general as hydrogen acceptors—a feat which has not been possible heretofore. In short, while ethylene is the preferred alkene, other straight and branched chain alkenes, such as propylene, the butenes, pentenes, hexenes, heptenes, octenes, decenes, dodecenes, and the like, and the cycloalkenes are deemed suitable as hydrogen acceptors in the process. The alkene preferably corresponds in skeletal structure to the alkene of the molecular complex initially present in the reaction system.

Various transition metal molecular complexes are deemed suitable for use as catalysts in the process. These include bis(alkene)cyclopentadienyl iridium complexes, diene cyclopentadienyl iridium complexes, bis(alkene)arene osmium complexes, diene arene osmium complexes, tris(alkene)cyclopentadienyl rhenium complexes, triene cyclopentadienyl rhenium complexes, diene alkene cyclopentadienyl rhenium complexes, bis(alkene)cyclopentadienyl rhodium complexes, diene cyclopentadienyl rhodium complexes, bis(alkene)cyclopentadienyl ruthenium complexes, diene cyclopentadienyl ruthenium complexes, tris(alkene)cyclopentadienyl technetium complexes, alkene arene iridium hydride complexes, alkene arene rhodium hydride complexes, bis(alkene)cyclopentadienyl ruthenium hydride complexes, diene cyclopentadienyl ruthenium hydride complexes, bis(alkene)cyclopentadienyl osmium hydride complexes, diene cyclopentadienyl osmium hydride complexes, bis(alkene)arene rhenium hydride complexes, diene arene rhenium hydride complexes, diene arene technetium hydride complexes, and similar materials, in which the cyclopentadienyl or arene groups may be unsubstituted or substituted with appropriate groups that do not prevent the desired transformation reaction from occurring, such as alkyl, fluoro, fluoroalkyl (trifluoromethyl, etc.), and the like. One particularly preferred class of complexes are the bis(alkene)pentamethylcyclopentadienyl iridium complexes, most especially bis(ethylene)pentamethylcyclopentadienyl iridium. These catalysts are stable in air and have good thermal stability characteristics rendering them especially suitable for commercial utilization. Other preferred classes of complexes, members of which have been investigated to date, include the bis(alkene)cyclopentadienyl iridium complexes, the bis(alkene)indenyl iridium complexes, the tris(alkene) pentamethylcyclopentadienyl rhodium complexes, and the bis(alkene)hexamethylbenzene osmium complexes.

The molecular complexes employed as catalysts pursuant to this invention may be represented by the general formula $$RML_nH_m$$

wherein R is a cyclopentadienyl group (which donates 5 electrons to the complex) or an arene group (which donates 6 electrons to the complex); M is a transition metal with an atomic number of 43, 44, 45, 75, 76 or 77; L is an alkene or cycloalkene group (each of which donates two electrons to the complex), a diene or cyclodiene group (which donates four electrons to the complex) or a triene or cyclotriene group (which donates six electrons to the complex); H is a hydrogen atom (which donates 1 electron to the complex; n is 1, 2 or 3; and m is zero or 1; the sum of the atomic number of M plus the number of electrons donated by R plus the total number of eleotrons donated by L and by H (if m is 1) being equal to the atomic number of the next higher rare gas relative to M.

Bis(ethylene)pentamethylcyclopentadienyl iridium reacts with paraffins photochemically at temperatures above and below 25° C., and thermally at 160° C. and above. Thus the process may be conducted by irradiating the reaction mixture with a source of ultraviolet light (sunlamp, sunlight, pure UV light, etc.) at any convenient temperature such as room temperature or sunlight-induced temperatures. Alternatively, the process may be conducted thermally by heating the reaction mixture to a temperature at which the transformation of paraffin to olefin occurs at a suitable reaction rate. In the case of thermal reactions using bis(ethylene) pentamethylcyclopentadienyl iridium complex as the catalyst and ethylene as the hydrogen acceptor, reaction is evident at about 170° C., and proceeds at a reasonable reaction rate at about 200° C. and above in a closed system under ethylene pressure. When employing the above transition metal complexes other than the iridium complexes, it is preferred to use thermolytic reactions, at suitable temperatures above about 200° C. although it may be possible in some cases to use lower reaction temperatures. Generally speaking, the process of this invention may be performed at any suitable pressure—subatmospheric, atmospheric, superatmospheric—so long as there is intimate contact among the components of the reaction mixture and the stability of the catalyst is not adversely affected. Thus with gaseous alkenes it is desirable to perform the reaction at a superatmospheric pressure, for example up to about 1,000 psi partial pressure or more. The temperatures used in the process may range upwards as high as 300° C. or more. Naturally one should not use a temperature and pressure that will lead to thermal decomposition of the catalyst, reactants or products of the particular reaction mixture being employed.

It is possible to prepare the transition metal complexes in situ by charging to the initial reaction system an appropriate cyclopentadienyl or arene molecular complex of the transition metal of atomic number 43–45 or 75–77, preferably iridium, having ligands that are displaced by the alkene. However when resorting to this practice, care should be exercised to select a complex which does not contain ligands that materially inhibit or suppress the desired paraffin-to-olefin transformation reaction. For example, complexes with hydrido or diene or triene ligands are suitable, as are complexes with carbonyl ligands, although the displaced carbonyl groups tend to exert a reaction-suppressing effect. Thus in any given case where it is desired to resort to use of an alkene cyclopentadienyl transition metal complex or alkene arene transition metal complex generated in situ in this manner, it is desirable to perform a few pilot experiments to insure that the released ligands do not adversely affect the desired reaction to any significant extent.

It is preferable to charge a transition metal complex such as a bis(alkene)cyclopentadienyl iridium complex or a diene cyclopentadienyl iridium complex to the reaction system in preformed condition. Most preferably the complex contains coordinated alkene corresponding to the free alkene to be used in the reaction. In this way the reaction mixture is devoid of significant amounts of extraneous components that would otherwise be released or formed during the reaction. However it is possible to use a complex in which the alkene initially differs from the free alkene to be used. In such cases the catalyst tends to equilibrate during the course of the reaction. Procedures that may be used or adapted for use in the synthesis of the transition metal catalysts such as the bis(alkene)cyclopentadienyl iridium complexes are reported for example by K. Moseley, J. W. Kang, P. M. Maitlis, *J. Chem. Soc.*, 1970, (A) 2875–2883, and by R. B. King, *Inorganic Chemistry*, Vol. 2 (1963) pp. 528–531.

A few exemplary catalysts which may be employed pursuant to this invention include
Bis(ethylene)cyclopentadienyl iridium
Bis(ethylene)methylcyclopentadienyl iridium
Bis(ethylene)dimethylcyclopentadienyl iridium
Bis(ethylene)trimethylcyclopentadienyl iridium
Bis(ethylene)tetramethylcyclopentadienyl iridium
Bis(ethylene)pentamethylcyclopentadienyl iridium
Bis(ethylene)ethylcyclopentadienyl iridium
Bis(ethylene)diethylcyclopentadienyl iridium
Bis(propylene)cyclopentadienyl iridium
Bis(propylene)pentamethylcyclopentadienyl iridium
Bis(butene)pentamethylcyclopentadienyl iridium
Bis(hexene)pentamethylcyclopentadienyl iridium
(1,3-butadiene)pentamethylcyclopentadienyl iridium
Bis(ethylene)pentamethylcyclopentadienyl rhodium
(Isoprene)pentamethylcyclopentadienyl rhodium
(Ethylene)hexamethylbenzene iridium hydride
(Ethylene)hexamethylbenzene rhodium hydride
Bis(ethylene)benzene osmium
Bis(ethylene)hexamethylbenzene osmium
(1,3-butadiene)toluene osmium
Bis(propylene)1,3,5-trimethylbenzene ruthenium
(1,3-hexadiene)benzene ruthenium
Tris(ethylene)cyclopentadienyl rhenium
(1,3,5-cyclooctatriene)cyclopentadienyl rhenium
Bis(ethylene)benzene rhenium hydride
(Isoprene)hexamethylbenzene rhenium hydride
Bis(ethylene)methylcyclopentadienyl ruthenium hydride
(1,3-butadiene)cyclopentadienyl ruthenium hydride
Bis(butene)cyclopentadienyl osmium hydride
(Isoprene)pentamethylcyclopentadienyl osmium hydride Among suitable catalyst precursors that have displaceable ligands and that may be used to form the catalyst in situ are the following:
Cyclooctadienetrimethylcyclopentadienyl iridium
Cyclooctadienepentamethylcyclopentadienyl iridium
Hydridopropenylpentamethylcyclopentadienyl iridium
Hydridodecenylpentamethylcyclopentadienyl iridium
Dicarbonylcyclopentadienyl iridium
Dicarbonylmethylcyclopentadienyl iridium
Dicarbonyldimethylcyclopentadienyl iridium
Dicarbonyltrimethylcyclopentadienyl iridium
Dicarbonyltetramethylcyclopentadienyl iridium
Dicarbonylpentamethylcyclopentadienyl iridium
Dicarbonylethylcyclopentadienyl iridium
Dicarbonyldiethylcyclopentadienyl iridium
Tetrahydridopentamethylcyclopentadienyl iridium
Cyclooctadienehexamethylbenzene osmium
Carbonyldihydrido benzene osmium
Carbonyldihydrido toluene osmium
Carbonyldihydrido hexamethylbenzene osmium
Tetrahydridohexamethylbenzene osmium
Dicarbonylhydrido cyclopentadienyl osmium
Cyclooctatrienepentamethylcyclopentadienyl rhenium
Tricarbonylcyclopentadienyl rhenium
Tricarbonylmethylcyclopentadienyl rhenium
Tricarbonylpentamethylcyclopentadienyl rhenium The reaction is preferably performed in bulk (i.e., with no auxiliary reaction solvent or diluent). However it may be conducted in solution in a suitable relatively inert liquid reaction medium such as neo-pentane, perfluorohexane, hexamethyldisiloxane, benzene, or the like. In many cases the paraffin or cycloparaffin reactant itself will serve as a solvent at least during the initial stages of the reaction. The reaction can be performed in the presence of such materials as triethylamine or water. On the other hand, dichloromethane has a detrimental effect.

Individual cyclic or acyclic paraffins or mixtures of different cyclic and/or acyclic paraffins may be used in the process. Likewise the feedstock may comprise mixtures of alkanes and alkenes, with or without other hydrocarbons (cycloparaffins, etc.), provided of course that the mixture has a sufficient alkane and/or cycloalkane content to make it economically feasible to subject it to processing in accordance with this invention. Use of cyclic and/or acyclic paraffinic hydrocarbons that are in the liquid state at the reaction temperature selected is preferred as this enables the reaction to be performed without use of an auxiliary reaction solvent or diluent. Thus paraffins and cycloparaffins of up to 100 or more carbon atoms may be used in the process. A preferred range is $C_6$ to $C_{24}$.

Aryl-substituted paraffins can also be used in the process. For example ethylbenzene, propylbenzene, 4-ethyltoluene, and 1,2-dimethyl-5-octylbenzene can be converted respectively to styrene, propenylbenzene, 4-methylstyrene and 1,2-dimethyl-5-octenylbenzene. Other aryl-substituted paraffins that may be used include 1-ethylnaphthalene, 1,4-diethylbenzene, isopropylbenzene, sec-butylbenzene, and many others. Thus another embodiment of this invention involves a process of transforming an arylalkane hydrocarbon catalytically into an arylalkene hydrocarbon which comprises reacting (i) an aromatic hydrocarbon having at least two adjacent carbon atoms in an alkyl substituent on an aromatic ring, each of such two carbon atoms having at least one hydrogen substituent thereon, with (ii) a transition metal molecular complex in the presence of free alkene so that olefinic hydrocarbon corresponding in skeletal configuration to the saturated hydrocarbon is formed, said complex catalyst having, at least at the commencement of the reaction, the formula $$RML_nH_m$$

wherein R is a cyclopentadienyl group (which donates 5 electrons to the complex) or an arene group (which donates 6 electrons to the complex); M is a transition metal with an atomic number of 43, 44, 45, 75, 76 or 77; L is an alkene or cycloalkene group (each of which donates two electrons to the complex), a diene or cyclodiene group (which donates four electrons to the complex) or a triene or cyclotriene group (which donates six electrons to the complex); H is a hydrogen atom (which donates 1 electron to the complex; n is 1, 2 or 3; and m is zero or 1; the sum of the atomic number of M plus the number of electrons donated by R plus the total number of electrons donated by L and by H (if m is 1) being equal to the atomic number of the next higher rare gas relative to M.

Proportions of the reaction components used are largely discretionary so long as there is enough alkene present to serve as acceptor for the hydrogen abstracted from the paraffinic reactant and to prevent catalyst decomposition.

The practice and advantages of this invention will be still further apparent from the following illustrative examples.

EXAMPLE I

A 50 mL bomb was charged with 3.88 mL of decane (dried over molecular sieves and distilled) and 30 mg of bis(ethylene)pentamethylcyclopentadienyl iridium. The resulting solution contained 0.39 mole percent catalyst. The bomb was flushed with dry ethylene to remove air and then charged with ethylene to an initial pressure of 150 psi. The contents of the sealed bomb (which initially included about 20 mmole each of decane and ethylene) were held at about 200° C. and 260 psi pressure for 60 hours. Analysis of the liquid reaction product by gas chromatography gave the following results (mole percentages):

1-decene: 0.61%
2-decene: 1.82%
3-decene: 2.00%
4- & 5-decenes: 2.13%
Total: 6.56%
Turnovers: 6.56/0.39=16.8

$^1$H NMR analysis of the liquid confirmed this turnover ratio. Gas chromatographic analysis of the ethylene gas removed from the bomb at the conclusion of the run showed 6.2 mole % of ethane.

EXAMPLE II

Bis(ethylene)pentamethylcyclopentadienyl iridium (30 mg) and decane (2.83 g) (pretreated with $H_2SO_4$ to remove olefins, passed through silica gel and distilled under nitrogen) were charged to a 45 mL screw top Parr bomb. The closed bomb was pressured to 150 psi with ethylene, shaken and the pressure released. The bomb was shaken again without ethylene pressure. This procedure was repeated several times to degas the solution. The bomb was then pressured with ethylene to 150 psi at room temperature and placed in a 250° C. bath. The temperature was held between 240° and 250° C. for 19 hours. The pressure at 246° C. was 340 psi. The bomb was allowed to cool. The liquid was clear and brownish-yellow. Some dark material coated the bottom of the bomb. 2.27 Grams of solution was recovered. Gas chromatography of the gas (ambient temperature, POROPAK Q 3 m×⅛ inch) showed 16.65, 16.92 and 18.36 area % ethane, on samples taken sequentially as the solution was outgassing. G. C. showed the product contained 16 weight percent decenes, the isomer distribution of which was as follows:

4- & 5-decene: 31.22%
3-decene: 30.25%
2-decene: 29.17%
1-decene: 9.58%

The run showed 40 turnovers of the reaction:

$$C_2H_4 + n\text{-}C_{10}H_{22} \rightarrow C_2H_6 + n\text{-}C_{10}H_{20}$$

An additional group of peaks appeared at higher retention time in the gas chromatographic trace of the liquid. Total area % of these peaks was 1%. They have about the same retention time as an authentic sample of 1,3-decadiene and thus the peaks are believed to represent isomeric decadienes.

EXAMPLE III

In this run, reaction was carried out photochemically between pentane and bis(ethylene)pentamethylcyclopentadienyl iridium in a sealed NMR tube. This iridium complex (10 mg) was added to an NMR tube attached to a vacuum stopcock. The air was evacuated from the tube and 0.5 mL of dry pentane was vacuum transferred into the tube. The system was allowed to stand at room temperature under ultraviolet light overnight. The pentane was removed by vacuum, and toluene-d8 NMR solvent was vacuum transferred to the tube. The tube was sealed and the contents subjected to $^1$H NMR. The NMR spectrum showed characteristic hydride and allylic resonances indicating attack by the complex on the C-H bonds of pentane, elimination of ethane and a second C-H insertion on coordinated pentene to produce isomeric forms of hydridopentenylpentamethylcyclopentadienyl iridium. Thus although free alkene was not used in this run, it demonstrates the operability of the photochemical process.

EXAMPLE IV

A sample of bis(ethylene)pentamethylcyclopentadienyl iridium was charged to a pipe bomb containing pentane. After 15 hours at 140° C., some free ethylene was noted in the $^1$H NMR spectrum. After 19 hours at 170° C., $^1$H NMR (90 MHz) showed new peaks in the olefin region. Thus operability of the thermolytic reaction between the complex and pentane was demonstrated even though free alkene was not included in the system as a hydrogen acceptor.

EXAMPLE V

A 45 mL PARR® screw cap type bomb was charged with dicarbonylpentamethylcyclopentadienyl iridium (30 mg, 78 micromoles) and decane (4.4 g). The solution was degassed by several pressurization/depressurization cycles with ethylene. The bomb was kept at 200° C. and 200 psig for 19 hours. No ethane was found in the gas phase. The temperature was raised to 250° C. and pressure of 240 psig. After 20 hours, the gas was 1.2% ethane. This corresponds to 2.4 turnovers.

EXAMPLE VI

A 45 mL PARR® screw cap type bomb was charged with cyclooctadienepentamethylcyclopentadienyl iridium (30 mg, 69 micromoles) and decane (3.45 g). The solution was degassed by repeated pressurization with ethylene to 150 psig and depressurization. The bomb was pressured to 150 psig and heated to 225° C. at which temperature the pressure was 310 psig. After 15 hours, the bomb was cooled and the gas sampled. The gas was 0.28% ethane indicating about one turnover.

EXAMPLE VII

Bis(ethylene)pentamethylcyclopentadienyl iridium (20 mg, 52 micromoles) and cyclooctane (8 mL, 59 mmoles) were charged to a 45 mL screw top PARR® bomb. The solution was degassed by several pressurization cycles with ethylene to 150 psig. The bomb was then pressured to 300 psig at 225° C. After 16 hours, the bomb was cooled and the gas sampled. Gas chromatographic analysis of the liquid indicated 0.54% cyclooctene.

EXAMPLE VIII

A 45 mL PARR® stainless steel screw cap bomb was charged with bis(ethylene)pentamethylcyclopentadienyl rhodium (35 mg, 118 μmol) and decane (3 mL, 14.8 mmol). The solution was degassed by repeated pressurization/depressurization cycles with ethylene. The bomb was then pressured to about 100 psig ethylene and heated to 220° C. at which temperature the pressure was 200 psig. After 24 hours, the liquid contained decenes at 7.96% by gas chromatography. This is 10 moles of decenes per mole of catalyst complex.

EXAMPLE IX

A mixture of decane (5 mL) and 3,3-dimethyl-1-butene (2 mL) was prepared. An aliquot of this solution (0.5 mL) and bis(ethylene)pentamethylcyclopentadienyl rhodium (10 mg) was added to a glass tube. The solution was freeze-degassed and the tube sealed. The sealed tube was heated to 220° C. for 16 hours. Gas chromatographic analysis of the solution showed 6.03% of the decane was converted to decenes.

EXAMPLE X

A sealed tube was prepared as in Example IX except that bis(ethylene)cyclopentadienyl iridium (10 mg) was used instead of bis(ethylene)pentamethylcyclopentadienyl rhodium. The sealed tube was heated to 220° C. for 16 hours. Gas chromatographic analysis of the solution showed 2.66% of the decane was converted to decenes.

EXAMPLE XI

A sealed tube was prepared and heated as in Example IX except that bis(ethylene)indenyl iridium (10 mg) was used instead of bis(ethylene)pentamethylcyclopentadienyl rhodium. Gas chromatographic analysis of the solution showed 0.73% of the decane was converted to decenes.

EXAMPLE XII

A sealed glass tube was prepared and heated as in Example IX except that bis(ethylene)pentamethylcyclopentadienyl iridium (10 mg) was used as the catalyst. Gas chromatographic analysis of the solution showed 2.91% of the decane was converted to decenes.

EXAMPLE XIII

A sealed glass tube was prepared as in Example IX except that in this case bis(ethylene)hexamethylbenzene osmium (6.5 mg) was used as the catalyst. After 17 hours at 220° C., gas chromatographic analysis of the solution showed 0.71% of the decane was converted to decenes.

EXAMPLE XIV

A solution of bis(ethylene)pentamethylcyclopentadienyl iridium (140 mg, 365 μmol) in decane (18.61 g, 0.131 mol) was prepared. An aliquot of this solution was placed in a glass tube with cyclohexene (.101 mL, 1 mmol). The solution was freeze-degassed and the tube was sealed. The sealed glass tube was then heated to 220° C. for 16 hours. Gas chromatographic analysis of the solution showed 0.28% of the decane was converted to decenes.

EXAMPLE XV

A sealed glass tube was prepared and heated as in Example XIV except that 2,3-dimethyl-2-butene (0.120 mL, 1 mmol) was added instead of cyclohexene. Gas chromatographic analysis showed 0.52% of the decane was converted to decenes.

EXAMPLE XVI

A sealed glass tube was prepared and heated as in Example XIV except that 3,3-dimethyl-1-butene (.120 mL, 1 mmol) was added instead of cyclohexene. Gas chromatographic analysis of the solution showed 2.97% of the decane was converted to decenes.

EXAMPLE XVII

A sealed glass tube was prepared and heated as in Example XIV except that 1-hexene (0.125 mL, 1 mmol) was used instead of cyclohexene. Gas chromatographic analysis of the solution showed 1.02% of the decane was converted to decenes.

EXAMPLE XVIII

A sealed glass tube was prepared containing bis(ethylene)pentamethylcyclopentadienyl iridium (10 mg, 26 mmol), decane (0.36 mL, 1.8 mmol), 3,3-dimethyl-1-butene (0.06 mL, 0.44 mmol) and benzene (0.2 mL). The tube was heated to 220° C. for 17 hours. Gas chromatographic analysis of the solution showed 7.1% of the decane was converted to decenes.

EXAMPLE XIX

A sealed glass tube was prepared and heated as in Example XVIII except that hexamethyl disiloxane (0.2 mL) was used instead of benzene. Gas chromatographic analysis of the liquid showed 6.23% of the decane was converted to decenes.

EXAMPLE XX

A sealed tube was prepared containing decane (0.7 g, 4.9 mmol), 3,3-dimethyl-1-butene (60 mg, 0.7 mmol), bis(ethylene)pentamethylcyclopentadienyl iridium (2.5 mg, 7.5 μmol) and perfluorohexane (0.3 mL). The tube was degassed and sealed. After 16 hours at 225° C., 3.1% of the decane had been converted to decenes.

EXAMPLE XXI

Ethylbenzene (3 mL, 24 mmol) and bis(ethylene) pentamethylcyclopentadienyl iridium (24 mg, 63 μmol) were charged to the 45 mL PARR bomb. The solution was degassed as usual, and pressured to 100 psig ethylene at room temperature. The bomb was heated to 222° C., 280 psi total pressure, for 16 hours. Gas chromatographic analysis of the gas shows 2.84 area % ethane. The liquid shows 0.83% styrene. This corresponds to about 3.2 turnovers. The identity of the styrene was confirmed by $^1$H NMR.

The bis(ethylene)hexamethylbenzene osmium utilized in Example XIII is exemplary of a new class of molecular complexes of osmium. The synthesis of such complexes is exemplified by the procedures set forth in Examples XXII and XXIII, below. In Example XXII the dimer of para-cymene osmium dichloride (see for example Synthesis of Triple Halide-Bridged Arene Complexes of Ruthenium (II) and Osmium (II), T. Arthur and T. A. Stephenson, *Journal of Organometallic Chemistry*, Vol. 208, 1981, pages 369–387) is reacted with hexamethylbenzene to produce the dimer of hexamethylbenzene osmium dichloride. Example XXIII illustrates the conversion of hexamethylbenzene osmium dichloride dimer into bis(ethylene)hexamethylbenzene osmium.

EXAMPLE XXII

The dimer of para-cymene osmium dichloride, [(p-cymene)OsCl$_2$]$_2$ (100 mg, 0.13 mmol) was placed in a 10 mL flask which was then filled with solid hexamethylbenzene (~7 grams). The air was removed by vacuum. The flask was then heated to 200° C. with stirring for two hours under nitrogen. The flask was cooled to room temperature, and the hexamethylbenzene was separated from the product by washing with pentane. The procedure was repeated to ensure complete conversion to [(C$_6$Me$_6$)OsCl$_2$]$_2$. The product was recrystallized from dichloromethane and characterized by $^1$H NMR. Yield 90 mg, 84%.

EXAMPLE XXIII

The dimer of hexamethylbenzene osmium dichloride, (C$_6$Me$_6$)OsCl$_2$]$_2$, (90 mg, 0.11 mmol) was placed in a 50 mL three neck flask. Ethanol (30 mL) was added and ethylene bubbled through the solution for ten minutes. Na$_2$CO$_3$ (50 mg, 0.5 mmol) was added to the solution and the mixture was heated to reflux with ethylene bubbling through the solution. After three hours, the mixture was cooled to room temperature and the volatiles removed by vacuum evaporation. The residue was extracted with pentane. The pentane extract was filtered through Florisil ® and evaporated to dryness to yield a yellow product, bis(ethylene)hexamethylbenzene osmium, which was characterized by $^1$H NMR. Yield: 87 mg, 86%.

It can thus be seen that this invention makes it possible to convert abundant paraffinic or cycloparaffinic hydrocarbons or any mixtures thereof into olefinic or cycloolefinic hydrocarbons or mixtures thereof. Depending on the saturated hydrocarbons used, the process thus may be used as a source of olefins for oxo process conversion to detergent and plasticizer alcohols as well as for making alkylated benzenes for the detergent industry. In addition, olefins suited for use in the manufacture of synthetic lubricants and lubricating oil additives (e.g., detergents and corrosion inhibitors) or for use as comonomers in the production of copolymers of ethylene can be formed by means of the process of this invention.

It will be understood and appreciated that the saturated hydrocarbons (i.e., the open chain paraffins and cyclic paraffins) used as reactants in the process may contain substituents or functionality so long as the conversion of the reactant to an olefin of the same skeletal configuration is not prevented by the substituents or functionality. For example, paraffins and cycloparaffins carrying a trialkylsilyl substituent, such as decyltrimethylsilane, dodecyltrimethylsilane, cyclooctyltrimethylsilane, and the like, are deemed suitable for use in the process. Similarly, ethylbenzene, propylbenzene and other paraffins and cycloparaffins having aromatic substituents may be used to produce such products as styrene, propenylbenzene and the like.

As noted above, the molecular complexes used as catalysts in the process can be preformed or formed in situ. In either case they will have, at least at the start of the reaction with the saturated hydrocarbon, a formula corresponding to that given hereinabove. Whether the complexes are transformed into other catalytic species during the course of the reaction has not been rigorously determined. The important point however is that if the catalyst used in the process (preformed or formed in situ) complies with the formula given hereinabove at least at the start of this reaction, the desired results can be obtained, irrespective of the precise reaction mechanism and catalytic transformations that may be occurring in the reaction system.

As this invention is susceptible to considerable variation in its practice without departing from its true spirit and scope, it is not intended that this invention be limited by the exemplifications given hereinabove. Rather, what is intended to be covered is encompassed by the appended claims and the equivalents thereof.

What is claimed is:

1. A process of transforming saturated hydrocarbon catalytically into olefinic hydrocarbon which comprises transferring hydrogen from the saturated hydrocarbon to an alkene via a transition metal molecular complex catalyst in the presence of free alkene so that olefinic hydrocarbon corresponding in skeletal configuration to the saturated hydrocarbon is formed, said complex catalyst having, at least at the commencement of the reaction, the formula $$RML_nH_m$$

wherein R is a cyclopentadienyl group, which donates 5 electrons to the complex, or an arene group, which donates 6 electrons to the complex; M is a transition metal with an atomic number of 43, 44, 45, 75, 76 or 77; L is an alkene or cycloalkene group, each of which donates two electrons to the complex, a diene or cyclodiene group, which donates four electrons to the complex or a triene or cyclotriene group, which donates six electrons to the complex; H is a hydrogen atom, which donates 1 electron to the complex; n is 1, 2 or 3; and m is zero or 1; the sum of the atomic number of M plus the number of electrons donated by R plus the total number of electrons donated by L and by H, if m is 1, being equal to the atomic number of the next higher rare gas relative to M; with the proviso that said complex is other than a bis(alkene) cyclopentadienyl iridium molecular complex.

2. A process of claim 1 wherein the free alkene and the alkene of the molecular complex are ethylene.

3. A process of transforming saturated hydrocarbon catalytically into olefinic hydrocarbon which comprises reacting the saturated hydrocarbon with a transition metal molecular complex in the presence of free alkene so that olefinic hydrocarbon corresponding in skeletal configuration to the saturated hydrocarbon is formed, said complex catalyst having, at least at the commencement of the reaction, the formula $$RML_nH_m$$

wherein R is a cyclopentadienyl group, which donates 5 electrons to the complex, or an arene group, which donates 6 electrons to the complex; M is a transition metal with an atomic number of 43, 44, 45, 75, 76 or 77; L is an alkene or cycloalkene group, each of which donates two electrons to the complex, a diene or cyclodiene group, which donates four electrons to the complex, or a triene or cyclotriene group, which donates six electrons to the complex; H is a hydrogen atom, which donates 1 electron to the complex; n is 1, 2 or 3; and m is zero or 1; the sum of the atomic number of M plus the number of electrons donated by R plus the total number of electrons donated by L and by H, if m is 1, being equal to the atomic number of the next higher rare gas relative to M; with the proviso that said complex is other than a bis(alkene) cyclopentadienyl iridium molecular complex.

4. A process of claim 3 wherein the reaction is performed in an inert organic solvent.

5. A process of claim 3 wherein the reaction is performed thermolytically under application of heat.

6. A process of claim 5 wherein the reaction is performed at superatmospheric pressure.

7. A process of claim 3 wherein said complex catalyst is a bis(alkene)cyclopentadienyl rhodium molecular complex.

8. A process of claim 3 wherein said complex catalyst is a bis(ethylene)cyclopentadienyl rhodium molecular complex.

9. A process of claim 3 wherein said complex catalyst is a bis(alkene)arene osmium molecular complex.

10. A process of claim 3 wherein said complex catalyst is a bis(ethylene)arene osmium molecular complex.

11. A process of claim 3 wherein the free alkene is an alkene or cycloalkene hydrocarbon containing up to about 8 carbon atoms.

12. A process of claim 3 wherein the free alkene and the alkene of the molecular complex are ethylene.

13. A process of transforming saturated hydrocarbon catalytically into olefinic hydrocarbon which comprises reacting the saturated hydrocarbon with a bis(alkene)pentamethylcyclopenta-dienyl rhodium molecular complex or a bis(alkene)hexamethylbenzene osmium molecular complex in the presence of free alkene so that olefinic hydrocarbon corresponding in skeletal configuration to the saturated hydrocarbon is formed.

14. A process of claim 13 wherein the molecular complex is bis(ethylene)pentamethylcyclopentadienyl rhodium.

15. A process of claim 13 wherein the molecular complex is bis(ethylene)hexamethylbenzene osmium.

16. A process of claim 13 wherein the saturated hydrocarbon is predominantly alkane hydrocarbon.

17. A process of transforming an arylalkane hydrocarbon catalytically into an arylalkene hydrocarbon which comprises reacting (i) an aromatic hydrocarbon having at least two adjacent carbon atoms in an alkyl substitutent on an aromatic ring, each of such 2 carbon atoms having at least one hydrogen substituent thereon, with (ii) a transition metal molecular complex in the presence of free alkene so that arylalkene corresponding in skeletal configuration to the arylalkane is formed, said complex catalyst having, at least at the commencement of the reaction, the formula $$RML_nH_m$$

wherein R is a cyclopentadienyl group, which donates 5 electrons to the complex, or an arene group, which donates 6 electrons to the complex; M is a transition metal with an atomic number of 43, 44, 45, 75, 76 or 77; L is an alkene or cycloalkene group, each of which donates two electrons to the complex, a diene or cyclodiene group, which donates four electrons to the complex, or a triene or cyclotriene group, which donates six electrons to the complex; H is a hydrogen atom, which donates 1 electron to the complex; n is 1, 2 or 3; and m is zero or 1; the sum of the atomic number of M plus the number of electrons donated by R plus the total number of electrons donated by L and by H, if m is 1, being equal to the atomic number of the next higher rare gas relative to M.

18. A process of claim 17 wherein said aromatic hydrocarbon is ethylbenzene whereby said arylalkene is styrene.

19. A process of claim 17 wherein said complex catalyst is a bis(alkene)cyclopentadienyl iridium molecular complex.

20. A process of claim 17 wherein said complex catalyst is bis(ethylene)pentamethylcyclopentadienyl iridium.

21. A process of claim 1 wherein the transition metal of said catalyst is rhodium.

22. A process of claim wherein the transition metal of said catalyst is osmium.

* * * * *

UNITED STATES PATENT AND TRADEMARK OFFICE
CERTIFICATE OF CORRECTION

PATENT NO.   : 4,751,344
DATED        : JUNE 14, 1988
INVENTOR(S)  : HOWARD W. WALKER

It is certified that error appears in the above-identified patent and that said Letters Patent is hereby corrected as shown below:

Cover page, references U.S. 4,042,609, August, 1977, Perrotti, not included.

Column 2, line 40, reads "eleotrons" and should read -- electrons --.

Column 9, line 53 reads "$(C_6Me_6)OsCl_2]_2$" and should read -- $[(C_6Me_6)OsCl_2]_2$ --.

Column 12, line 4, reads ". . . cyclopenta-dienyl . . ." and should read -- . . . cyclopentadienyl . . . --.

Column 12, line 56 reads "Claim wherein" and should read -- Claim 1 wherein --.

Signed and Sealed this

Thirty-first Day of October, 1989

Attest:

DONALD J. QUIGG

*Attesting Officer*    *Commissioner of Patents and Trademarks*